US006890550B1

(12) United States Patent
Jorgensen

(10) Patent No.: US 6,890,550 B1
(45) Date of Patent: May 10, 2005

(54) METHOD OF PREVENTING PARTURIENT HYPOCALCEMIA IN ANIMALS AND COMPOSITIONS USED THEREIN

(75) Inventor: Rolf Jess Jorgensen, Farum (DK)

(73) Assignee: RJ Innovation, Farum (DK)

( * ) Notice: Subject to any disclaimer, the term of this patent is extended or adjusted under 35 U.S.C. 154(b) by 0 days.

(21) Appl. No.: 09/527,680

(22) Filed: Mar. 17, 2000

Related U.S. Application Data
(60) Provisional application No. 60/161,919, filed on Oct. 28, 1999.

(30) Foreign Application Priority Data

Mar. 18, 1999 (DK) .......................................... 1999 00380
Sep. 30, 1999 (DK) .......................................... 1999 01395

(51) Int. Cl.$^7$ .............................................. A23K 1/175
(52) U.S. Cl. ....................... 424/442; 424/435; 424/438; 424/451; 424/458; 424/461; 424/464; 424/474; 424/480; 424/489; 424/494; 424/683; 424/684; 424/724
(58) Field of Search ................................. 424/434, 435, 424/438, 442, 451, 456–463, 474–482, 489–502, 78.01, 684, 690, 691, 724, 464, 683

(56) References Cited

U.S. PATENT DOCUMENTS

| | | | |
|---|---|---|---|
| 3,184,381 A | | 5/1965 | Ashmead |
| 3,908,020 A | | 9/1975 | Schroeder |
| 4,931,290 A | | 6/1990 | Rebhan |
| 5,082,662 A | * | 1/1992 | Laurent et al. ............. 424/442 |
| 5,277,896 A | * | 1/1994 | Balkus, Jr. ..................... 424/9 |
| 5,360,823 A | | 11/1994 | Griffel, Jr. et al. |
| 5,393,535 A | | 2/1995 | Kjems |
| 5,560,920 A | | 10/1996 | Goff et al. |
| 5,631,289 A | | 5/1997 | Abele |
| 5,906,842 A | * | 5/1999 | Sato et al. ..................... 426/2 |
| 5,912,030 A | * | 6/1999 | Huzinec et al. ................ 426/3 |
| 5,958,464 A | | 9/1999 | Register |

FOREIGN PATENT DOCUMENTS

| | | |
|---|---|---|
| DE | 1255466 | 11/1967 |
| GB | 1029200 | 5/1966 |
| GB | 2 058 564 A | 9/1980 |
| HU | 26 290 A | 12/1983 |
| JP | 63-056255 A | 3/1988 |

OTHER PUBLICATIONS

Jørgensen, Rolf Jess, Calciumklorid til køer. Bivirkninger efter peroral indgivelse—En foreløbig meddeleise, Dansk VetTidsskrift, 1990, 73, 3½, pp. 140–141 and English Abstract.

Oetzel, Garrett R., Meta–Analysis of Nutritional Risk Factors for Milk Fever in Diary Cattle, J. Dairy Sci, 1991, 74:3900–3912.

Glawischnig, E, Zur Resorption peroral verabreichter Kalziumsalze, Internationale Tagung Uber Rinderkrankheiten, Wien 1962, pp. 19–20 and English Abstract.

Oetzel, Garrett R., Improving Reproductive Performance in Dairy Cattle Via Milk Fever Prevention, The Bovine Proceedings, No. 28, 1996.

Enevoldsen, Carsten, Nutritional Risk Factors for Milk Fever in Dairy Cattle: Meta–analysis Revisited, Acta Vet. Scand. 1993, Suppl 89, 131–134.

Lomba et al., Calcium digestibility in cows as influenced by the excess of alkaline ions over stable acid ions in their diets, Br. J. Nutr. (1978) 39, 425–429.

Dishington, I.W. and Bjøemstad, J., Prevention Of Milk Fever By Dietary Means. The Effect Of A Concentrate Fortified With Mineral Salts, Acta Vet. Scand. 1982, 23, 336–343.

Jørgensen, R.J. et al., 1990. Sequelae To Oral Calcium Chloride Gel Dosing Of Cows. Proceedings, XVI Word Buiatrics Congress, 13.17. Aug. 1990, Salvador, Brazil, pp. 511–515.

Ramberg, C.F., Phang, J.M. and Kronfeld, D.S., A Compartmental Model of Calcium Metabolism in Cows, In: Partutrient hypocalcemia, Academic Press, New York, (1970) pp. 119–134.

Van't Klooster, A.Th., Adaptation of calcium absorption from the small intestine of dairy cows to changes in the dietary calcium intake and at the onset of lactation, Z. Tierphysiol., Tierernährg. u. Futtermittelkde, (1976) 37 169–182.

J.T. Schonenwille et al., "Hypocalcemia Induced by Intravenous Administration of Disodium Ethylenediaminotetraacetate and its Effect on Excretion of Calcium in Urine of Cows Fed a High Chloride Diet", Journal of Dairy Science, vol. 82, No. 6, 1999, pp. 1317–1324 (XP–002123422).

R.J. Jørgensen et al.: "Induced Hypocalcemia by Na$_2$EDTA Infusion. A review." Journal of Veterinary Medicine, vol. 46, No. 7, 1999, pp. 389–407 (XP–000853976).

LSB Mellau et al.: "Standardization and interpretation of experimental (Na$_2$–EDTA induced) hypocalcaemia in cows." Production diseases in farm animals, 10$^{th}$ international ICPD conference 1998, ed: Th. Wensing, Published by Wageningen Press, p. 238.

(Continued)

Primary Examiner—Neil S. Levy
(74) Attorney, Agent, or Firm—Iver P. Cooper

(57) ABSTRACT

Method of preventing parturient hypocalcemia and milk fever (parturient paresis) in lactating animals comprising administering to the animal during the dry period a compound which reduces absorption of calcium from the drinking water and/or from the ration of said animal. The method is based on the powerful, natural calcium regulating mechanisms and is applicable under commercial farming conditions.

18 Claims, 7 Drawing Sheets

OTHER PUBLICATIONS

BL Smith et al.: "Hypocalcaemia associated with high dose rates of zinc oxide to lactating dairy cows", New Zealand Vet. Journal, vol. 32, 1984, pp 48–50.

IW Dishington, "Prevention of Milk Fever (Hypocalcemia Paresis Puerperalis) by Dietary Salt Supplements", Acta Vet Scand, vol. 16, 1975, pp 503–512.

TJ Rosol, "Pathophysiology of Calcium Metabolism," Vet Clinical Pathology, vol. 24, No. 2, pp 49–62.

C. Wang et al., "Effects of Ammonium Chloride and Sulfate on Acid–Base Status and Calcium Metabolism of Dry Jersey Cows", J. Dairy Sci, vol. 75, 1992, pp. 820–828.

K. Hove, "Milk fever prevention and calcium homeostasis around calving in the dairy cow", Irish Vet. News, Mar. 1987, pp. 24–28.

International Search Report for PCT/DK 00/00108.

* cited by examiner

Fig. 4

The size of changes in serum Ca, mmol/l

Dose number

- lact+ZnO1
- lact+ZnO2

US 6,890,550 B1

METHOD OF PREVENTING PARTURIENT HYPOCALCEMIA IN ANIMALS AND COMPOSITIONS USED THEREIN

This application claims the benefit, under 35 USC 119(e), of 60/161,919, filed Oct. 28, 1999.

FIELD OF THE INVENTION

The present invention provides a method of preventing parturient hypocalcemia in animals and in particular there is provided compositions which can be administered to the animals during the dry period to prevent hypocalcemia and milk fever.

TECHNICAL BACKGROUND AND PRIOR ART

Parturient hypocalcemia is a metabolic disease of lactating animals, such as dairy cows, and occurs as subclinical hypocalcemia around calving and in early lactation and in severe cases lactating animals contract clinical milk fever (parturient paresis). The lactation cycle of a dairy cow extends for approximately 10 month of the year immediately subsequent to calving. Lactation by dairy cows is at a minimum during the two month immediately prior to calving, and the dairy cows are normally not milked during this "dry period". The act of calving induces lactation in the dairy cow, and milk production is at a peak by 4–6 weeks thereafter.

During the dry period, the dairy cow has a low demand for calcium, and is thus able to absorb sufficient calcium via the digestive tract by simple passive diffusion. During lactation the demand for calcium is high, which leaves the cow in a negative calcium balance, which results in the activation of the vitamin D-dependent complex mechanisms. The lactating cow is thus capable of increasing the utilisation of the feed ration calcium by increasing absorption from the digestive tract and by resorbing calcium from the skeletal system via the blood. By these active mechanisms the lactating cow is capable of covering up to 80% of its demand for calcium during lactation (Klooster, 1976). Therefore, lactating animals are capable of preventing hypocalcemia to occur due to these powerful natural defence mechanisms almost regardless of the calcium intake via the feed.

However, during the dry period these natural defence mechanisms are deactivated, as the demand for calcium is low. Upon calving and onset of lactation there is an immediate demand for high levels of calcium to be supplied via the blood circulation to the mammary glands for milk production. The calcium regulating mechanisms are not prepared for this sudden demand for calcium in the high yielding dairy cow, and it must thus contract hypocalcemia and milk fever. Symptoms of milk fever, such as lowering of body temperature, usually become manifest within one day before and four days after calving.

Extensive research has been conducted to develop methods for preventing or treating milk fever. It has been observed that the risk for milk fever is reduced when the acid-base balance of the dairy cow is manipulated by acidifying dietary ration composition (Dishington, 1982). Presently, a method based on this principle is widely used in the USA. However, acidification of dairy cows is unnatural, since urine from ruminants normally is alcaline. Furthermore, overdosage has been reported.

Another approach of preventing milk fever is the peroral drenching with calcium chloride around calving (Jørgensen, 1990). The effect of this method is interpreted as a simple calcium diffusion through the wall of the forestomach and through the wall of the small intestine. However, there are several drawbacks associated with this method. The dairy cows have to be handled and dosed individually, which involves the above mentioned problems. Furthermore, the precise calving time of the cow must be known, because the first drenching is recommended to be carried out a few hours before calving.

Injection of a synthetic D-vitamin preparation in large doses has been suggested for the prevention and/or treatment of milk fever. Although this method is documented to be effective, it is not allowed in many countries. Another suggestion involves continuous milking, which will prevent milk fever, as the calcium regulating mechanisms are constantly activated. However, this method is only applicable to single cows which are known or suspected to contract milk fever, but it is not feasible at a herd level.

Ramberg et al. (1970) observed that milk fever can be controlled and/or eliminated by administering a low calcium dietary ration to dairy cows during the weeks immediately prior to calving. By feeding a low calcium dietary ration, the cow is left in a negative calcium balance, which results in the activation of its natural calcium regulating mechanisms. Unfortunately, there are many problems associated with this method. For example, most of the cattle feed, such as alfalfa and other legumes, contain too high levels of calcium to bring the dry cow in a negative calcium balance. Furthermore, the method presents a substantial problem when dealing with a large herd. To solve the above first mentioned problem, U.S. Pat. No. 3,908,020 discloses a complete, calcium-limited feed ration. However, this method implies the purchase of rather expensive feed, which is not feasible under commercial dairy farming conditions, when the farmer is using his home-grown crops for feeding.

In view of the foregoing it is evident that these currently used methods of preventing hypocalcemia involve several problems in modern farming. It is thus an important objective of the present invention to provide a novel composition and method to prevent hypocalcemia in lactating animals. The disclosed method has the advantage that its effect is based on the powerful, natural calcium regulating mechanisms of animals and at the same time it is applicable under commercial dairy farming conditions.

SUMMARY OF THE INVENTION

Accordingly, it is the primary objectives of the present invention to provide a novel method of preventing hypocalcemia in lactating animals and a composition which is useful in such a method.

Thus, in a first aspect, the invention pertains to a method of preventing hypocalcemia in a lactating animal, comprising administering to the animal during at least part of the dry period an effective amount of a compound which reduces absorption of calcium from drinking water and/or from the ration of said animal.

There is also provided a composition for preventing hypocalcemia in a lactating animal, comprising a compound which reduces the absorption of calcium from the drinking water and/or from the ration of said animal.

In a further aspect, the present invention relates to the use of the above composition for the prevention of hypocalcemia in a lactating animal, comprising administering to the animal during at least part of the dry period an effective amount of a compound which reduces the absorption of calcium from the drinking water and/or from the ration of the animal.

In yet another aspect the invention pertains to a method of using the above composition for the prevention of hypocalcemia in a lactating animal, the method comprising administering to the animal during at least part of the dry period an effective amount of a compound which reduces the absorption of calcium from the drinking water and/or from the ration of the animal according to the above method.

In a still further aspect, the invention relates to the use of a calcium-binding compound or a composition in the manufacturing of a medicament for preventing hypocalcemia in a lactating animal.

DETAILED DISCLOSURE OF THE INVENTION

It is an essential feature of the method for preventing hypocalcemia in lactating animals which is provided herein that the biological effect of the compound used in the method is capable of stimulating or triggering the natural calcium regulating defence mechanism of the animal. Through this stimulating ability on the calcium metabolism before the onset of lactation, the used compound will render the animal well prepared to resist any threatening parturient hypocalcemia.

Thus, the method according to the invention comprises administering to the animal during at least part of the dry period an effective amount of a compound which reduces absorption of calcium from drinking water and/or from the ration of said animal. As used herein, the expression "lactating animal" designates the mammalian class of the animal kingdom such as e.g. cow, pig, horse, cat, sheep, goat, buffalo, camels, monkey or man. Thus, the term "ration" relates both to "food" and "feed" given prior to the onset of lactation of said animal.

An advantageous feature of the method according to the invention is that the precise parturition time of the animal does not need to be known, as the compound can be given to the animal at any time during the dry period, such as at least about 1 to 4 weeks prior expected parturition, including at least about 2 to 3 weeks prior to expected parturition.

In order to be present in the gastrointestinal tract of the animal the compound is administered orally. The compound may be administered with the feed or water or administered alone, as long as the time interval between administration of the compound and intake of calcium-containing feed and/or water is not too long. It is in this respect important that a sufficient amount of the compound is present in the gastrointestinal tract simultaneously with the free ionized calcium, which would otherwise be available for absorption.

The amount of compound administered must be sufficient to obtain the preventive effect. It is preferred that the compound is administered in an amount of at least 10 g per animal per day depending on the body weight of the animal. More preferred at least 50 g of the compound is administered per day per animal. In particular in respect of zeolites and EDTA-compounds it may be preferred to administer at least 100 g per day per animal. Normally up to about 1000 g per day per animal is administered.

In presently preferred embodiments, the method according to the invention comprises administering to the animal during at least part of the dry period an effective amount of a calcium-binding compound. It will be understood that the expression "calcium-binding compound" refers to compounds which are capable of binding free (ionised) calcium in aqueous solution.

Calcium-binding compounds which are useful in the above method can be any compounds which are capable of binding free calcium in the animal gastro-intestinal tract whereby the free calcium cannot be absorbed by the animal. Thereby, the natural calcium regulating defence mechanism of the animal is triggered. Such compounds include compounds that are either digestible when given in an unprotected form or non-digestible in the rumen selected from the group consisting of oxalic acid, sodium oxalate, phytic acid, a phytate, a clay mineral including zeolite, sodium diethylene acetic acid, ethylenediaminetetraacetic acid (EDTA) and its sodium salts $Na_2EDTA$ and $Na_4EDTA$, trisodium nitrilotriacetate monohydrate, trisodium nitriloacetate, pentasodium diethylenetriaminepentaacetate, trisodium N-hydroxyethylethylenediaminetriacetate, citric acid, a citrate, a polyphosphate, a tripolyphosphate, an orthophosphate and a cellulose phosphate and calcium-free derivatives of any such compounds.

In a preferred embodiment the calcium-binding compound is selected from the group consisting of a clay mineral including zeolite, ethylenediaminetetraacetic acid (EDTA) and its sodium salts $Na_2EDTA$ and $Na_4EDTA$, a polyphosphate, a tripolyphosphate, an orthophosphate and a cellulose phosphate and a calcium-free derivative of any such compounds.

In a more preferred embodiment the the calcium-binding compound is selected from the group consisting of a clay mineral including zeolite and a calcium-free derivative of any such compounds.

In a presently preferred embodiment, the method according to the invention comprises administering to the animal during at least part of the dry period an effective amount of a compound which has a competitive effect on the absorption of calcium from the drinking water and/or from the ration of said animal through the wall of the gastro-intestinal tract. It is contemplated that such compounds will compete with the calcium of the dry animal dietary ration by being preferred by the calcium absorbing mechanism. Examples of such compounds are zinc compounds including zinc oxide, $ZnCl_2$ and $ZnSO_4$.

It is, as mentioned above, of considerable commercial interest to provide a method of preventing hypocalcemia in lactating animals which is applicable under commercial farming conditions. In a highly convenient embodiment of the method according to the invention, the compound used in the method is contained in a composition which is in the form of a premix, a liquid or a powder. It is contemplated that such a composition can easily be administered to the dry animal perorally for example in a specific embodiment, it is added to the drinking water and/or the ration of the dry animal.

In a further aspect of the invention there is provided a composition, which is used in the above method for preventing hypocalcemia in a lactating animal. The composition comprises, in a form suitable for peroral administration, a compound which reduces the absorption of calcium from the drinking water and/or from the ration of said animal.

In an advantageous embodiment of the composition according to the invention the compound is any of the above calcium-binding compounds. It will be understood that it is possible to have a mixture of two or more calcium-binding compounds in the same composition.

In one useful embodiment of the composition according to the invention, the compound has a competitive effect on the absorption of calcium from drinking water and/or from the ration of the dry animal. Typical examples of such compounds are zinc compounds such as e.g. zinc oxide, $ZnCl_2$ or $ZnSO_4$.

To prevent degradation of the compound before reaching the suitable place of action in the gastro-intestinal tract the compound according to the invention may be in encapsulated form. The compounds which are used in the above compositions may be encapsulated by any appropriate encapsulating material. In specific embodiments of the invention, a useful compound for the encapsulation is a compound selected from the group consisting of a fat, a non-calcium derivative of a fat such as a soap and a stearate, a protein, a polysaccharide, a cellulose and a derivative of any such compound, a gum, a glycol and gelatine.

In an interesting embodiment, the composition according to the invention comprises compounds which are encapsulated by a calcium-free membrane material, which at the body temperature of the lactating animal is solid at a pH value above 4.0 but which under these conditions dissolves at pH below 4.0. It is contemplated that compounds encapsulated in such a membrane material can be transported through the rumen of a ruminant without being dissolved, and thus is not dissolved until it arrives in the gastrointestinal system after passage of the forestomachs of the ruminant.

In particular in relation to zink compounds encapsulated compounds are preferred.

In a highly convenient embodiment of the invention, the composition is in the form of a premix, a liquid and a powder, or it in the form of granules, a pellet, a dragee, a tablet, a pill, or a capsule. A composition provided in such a form will be advantageous from a users point of view, since it can easily be administered to the dry animal. In a specific embodiment, the composition is added to or mixed into the drinking water and/or in the ration of the lactating animal. It is evident that such a composition is very useful, when farmers use their own grown crops as feed.

In useful embodiments, the composition according to the invention is a composition comprising the above compounds and at least one further ingredient such as a vitamin, a mineral and a carrier. A useful example of such a carrier is e.g. bran. Further ingredients can be selected from a sugar, a stabilising agent and a colouring agent. Additionally, the composition is calcium-free and non-acidifying, i.e. the composition is not causing biological acidification of the animal's urine.

In further aspects, the invention relates to the use of a composition according to the invention, comprising administering to the animal during at least part of the dry period an effective amount of a compound which reduces the absorption of calcium from the drinking water and/or from the ration of the animal.

In a still further aspect the invention relates to the use of a composition according to the present invention for the prevention of hypocalcemia in a lactating animal.

Furthermore, there is provided a method of using a composition according to the invention for the prevention of hypocalcemia in a lactating animal, the method comprising administering to the animal during at least part of the dry period an effective amount of a compound which reduces the absorption of calcium from the drinking water and/or from the ration of the animal according to the method of the present invention.

In addition, the present invention relates to the use of a calcium-binding compound or a composition according to the invention in the manufacturing of a medicament for preventing hypocalcemia in a lactating animal.

The invention will now be described in further details in the following non-limiting examples and the drawings wherein FIG. 1 shows the response of three cows (Nos. 169, 170 and 168) to repeated short-term periods of hypocalcemia induced by EDTA test infusions. The other three cows (Nos. 172, 175 and 176) were dosed daily with anionic salts prior to the EDTA-testing. Cal=ionised calcium in the blood;

FIG. 2 shows the blood calcium response to oral administration of zinc oxide in pairs of lactating as well as non-lactating cows. A total of four treatments were given at one-week intervals. Arrows indicate time of treatment;

FIG. 4 shows the blood calcium response of two lactating cows to the four doses of zinc oxide expressed in terms of the extent of the drop in blood calcium;

Figure 5:
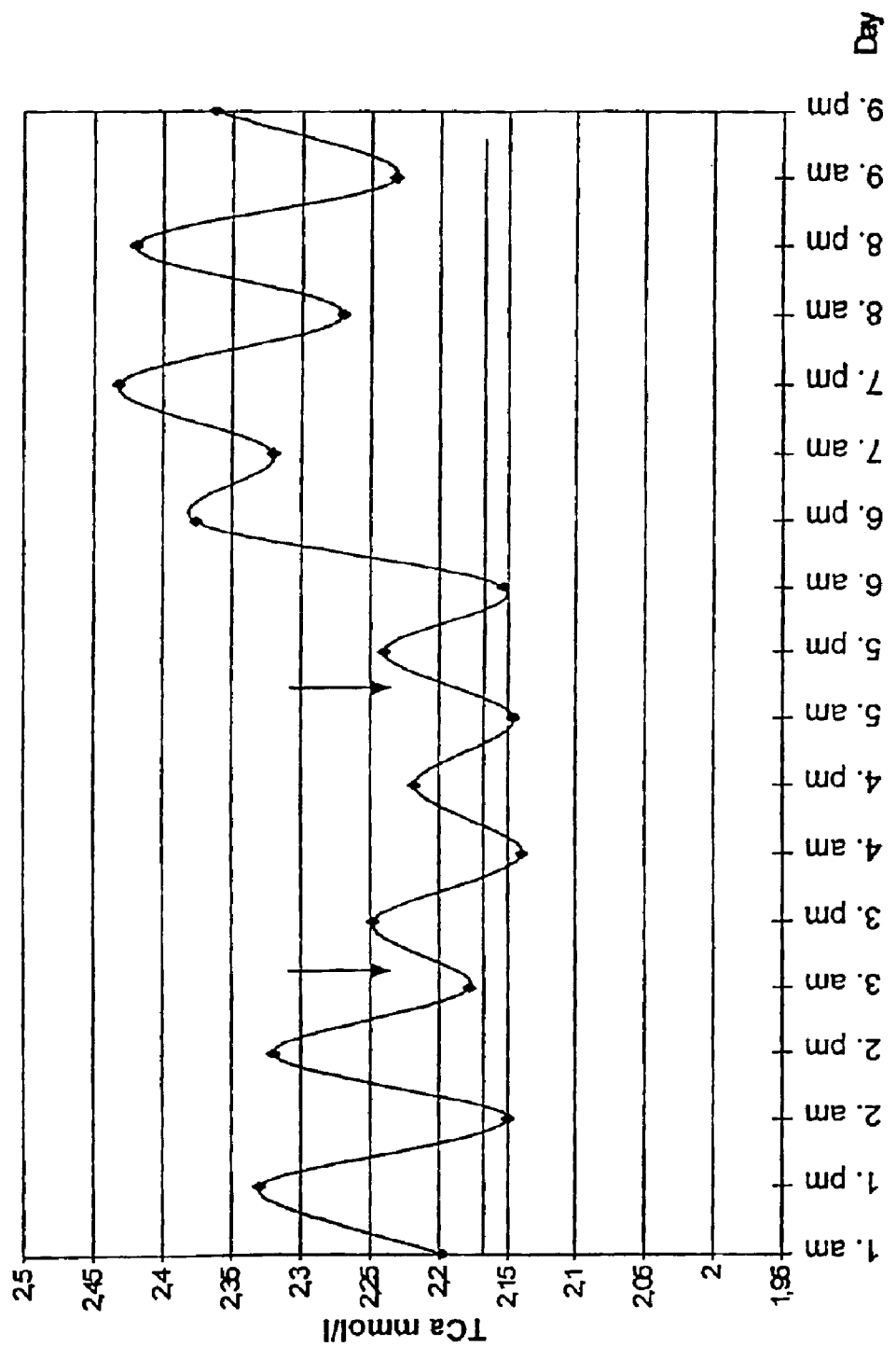
Figure 6:
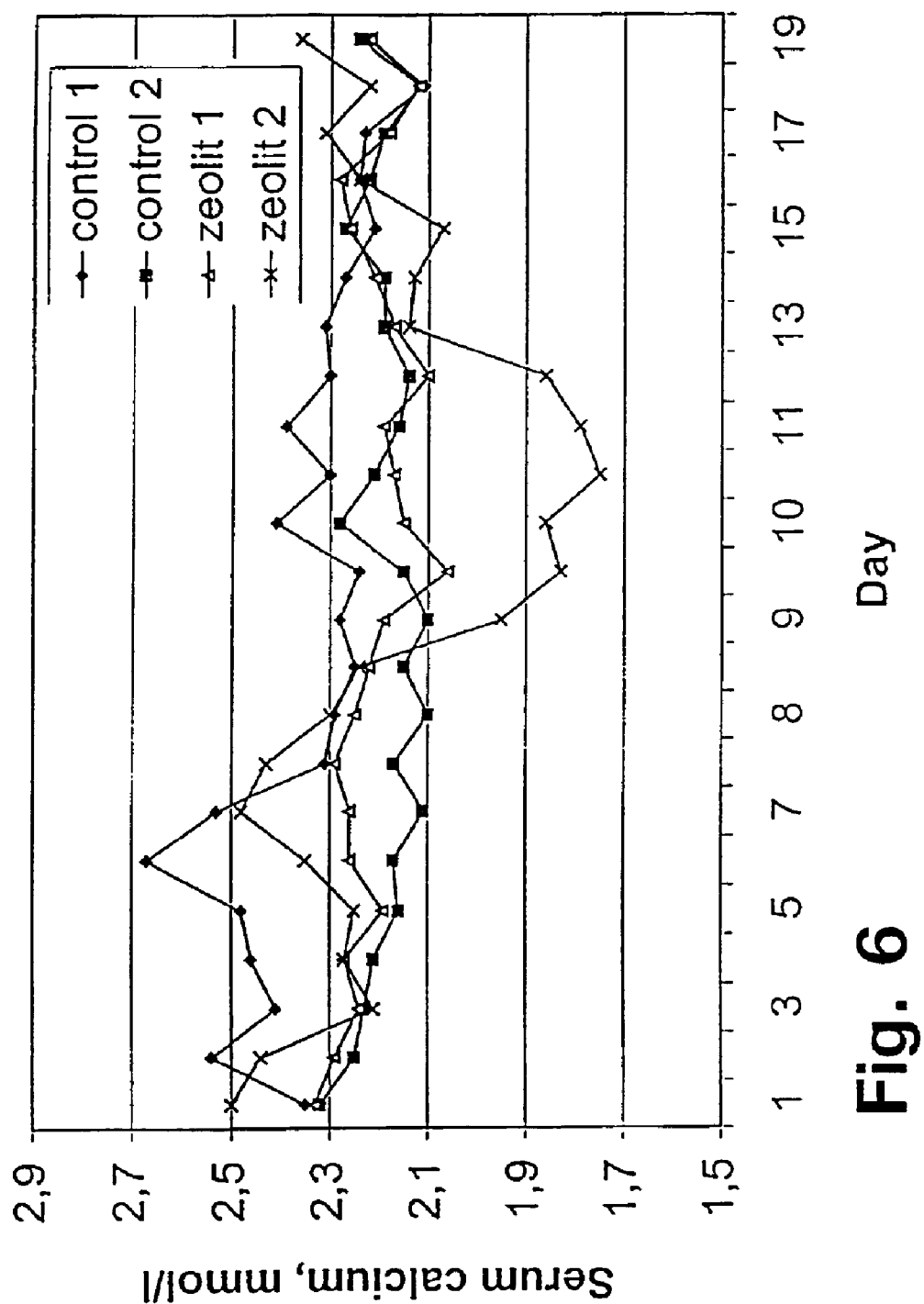

FIG. 5 shows the blood calcium of five dairy cows in late lactation. The graph shows the response, in form of suppression of the daily increase of blood calcium, during administration of 2×500 g of a synthetic zeolite A (sodium aluminium silicate) per day, and a late response in form of "overshooting" at 24 hours after the last administration and onwards; and FIG. 6 shows the blood calcium of four non-pregnant dry cows: Two untreated controls and two treated with 2 kg zeolite A (sodium aluminium silicate) once a day on day 8, 9, 10 and 11.

FIG. 7 shows the serum calcium of A) 7 untreated cows, and B) 7 cows treated with sodium-aluminosilicate type A zeolite.

EXAMPLE 1

Repeated EDTA-Infusions in Non-Lactating (Dry) Cows 1.1. Introduction

It is known that hypocalcemia can be induced experimentally by slow intravenous infusion of EDTA. Such induced hypocalcemia is performed for a variety of reasons, as reviewed by Jorgensen et al. (1999).

1.2. Materials and Methods

To investigate the induction of hypocalcemia by intravenous infusion of EDTA in cows, 6 non-lactating (dry) cows were used in this study. Three of these cows were untreated (cow Nos. 168, 169 and 170) and the other three cows (cow Nos. 172, 175 and 176) had been subjected to a pre-treatment consisting of daily doses of anionic salts (Wang and Beede, 1992). This pre-treatment is known to be effective in preventing milk fever. The latter cows were rumen fistulated to facilitate precise daily dosages of the anionic salts.

All cows were tested for resistance to hypocalcemia by the EDTA-infusion technique. A total of 8 EDTA-tests were performed per cow according to the standardised method of Mellau et al. (1998), at 10 days intervals. With the standardised test, infusion of EDTA was performed until the cow went down involuntarily, due to muscle weakness caused by the induced hypocalcemia. The time taken from this point and until the cow regained normal blood calcium concentration, which is defined as an ionised blood calcium value above 1 mmol/l, was recorded. This time is considered to represent the cows' calcium mobilisation rate and therefore also the cows' ability to resist hypocalcemia. The infusion periods varied between individual cows, but were typically in the range of 2–4 hours. The total time exposed to hypocalcemia during one test, i.e. during infusion plus during recovery, was in the range of 4–8 hours.

1.3 Results

Figure 1:
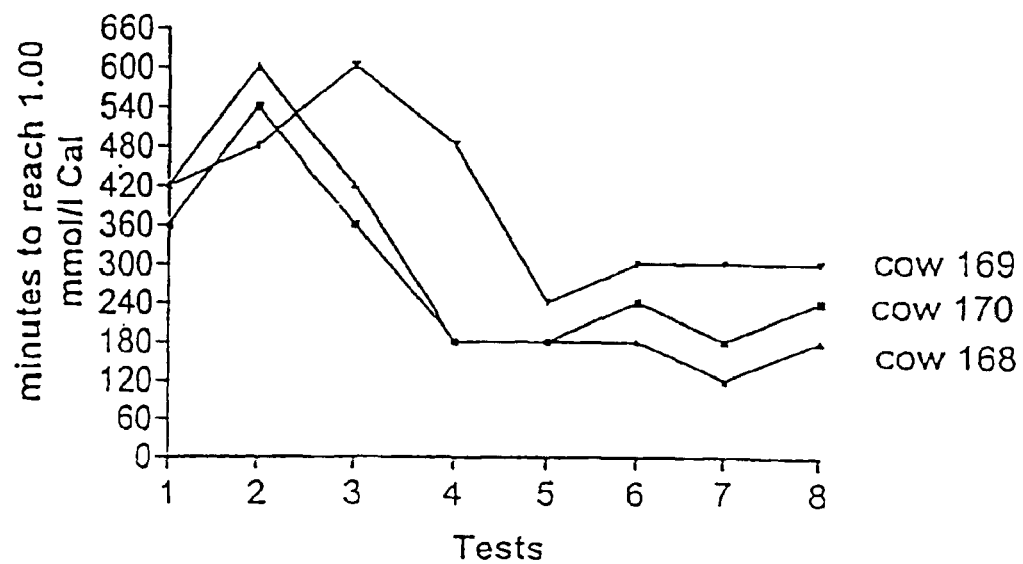
Figure 1:
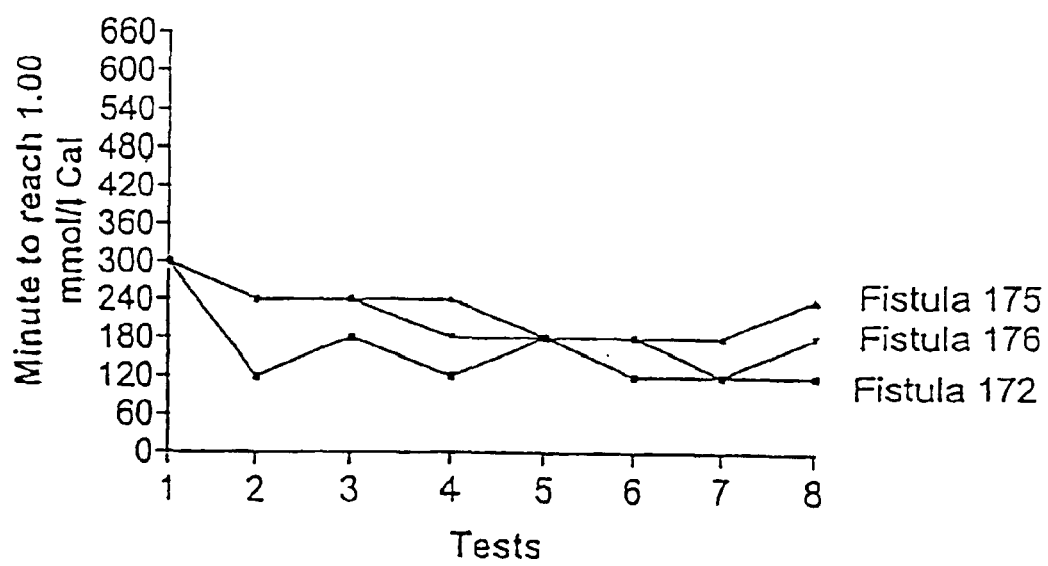

It is obvious from FIG. 1 that the time it took to regain normal blood calcium concentration greatly improved in the three untreated control cows after three infusions in terms of reduced recovery time and therefore a fall in the graphs for individual cows indicated increased resistance to hypocalcemia. For comparison, the results of three other cows tested in the same way in the same experiment, but after a 1-day period of daily anion treatment prior to EDTA-testing, are also shown. As would be expected the recovery time for these cows was relatively short already at the first EDTA-test due to the treatment prior to the test period.

1.4 Discussion

Hypocalcemic episodes of a few hours duration, induced three times at 10-day intervals, resulted in shortened recovery periods at later similar challenges. The effect was of the same magnitude as that recorded after daily anion supplementation, which is a well-known milk fever preventive method.

EXAMPLE 2

Repeated Zinc Oxide Administration in Cows 2.1 Introduction

Until now, the only known way of inducing hypocalcemia via the oral route (by mouth) has been that recorded as an undesired side-effect of administration of zinc in the form of zinc oxide to cattle and small ruminants (Smith et al. 1984). Such treatment is given against facial eczema in sheep and cattle. The possible invasive effect of repeated challenges towards resistance to hypocalcemia was examined in this study involving lactating as well as non-lactating (dry) cows.

2.2 Materials and Methods

Six dairy cows were used in this study: Two lactating cows and two dry cows were treated with zinc oxide by mouth at 120 mg/kg body weight, whereas two lactating cows served as untreated controls. Four doses of zinc oxide were given to the treated cows at one-week intervals. Venous blood samples were taken and serum stored at −37° C. for later total calcium determinations. For this purpose blood samples were taken daily from all six cows one hour after morning feeding. Extra samples were taken 5, 11, 23 and 35 hours after zinc oxide administration.

2.3 Results

Figure 2:
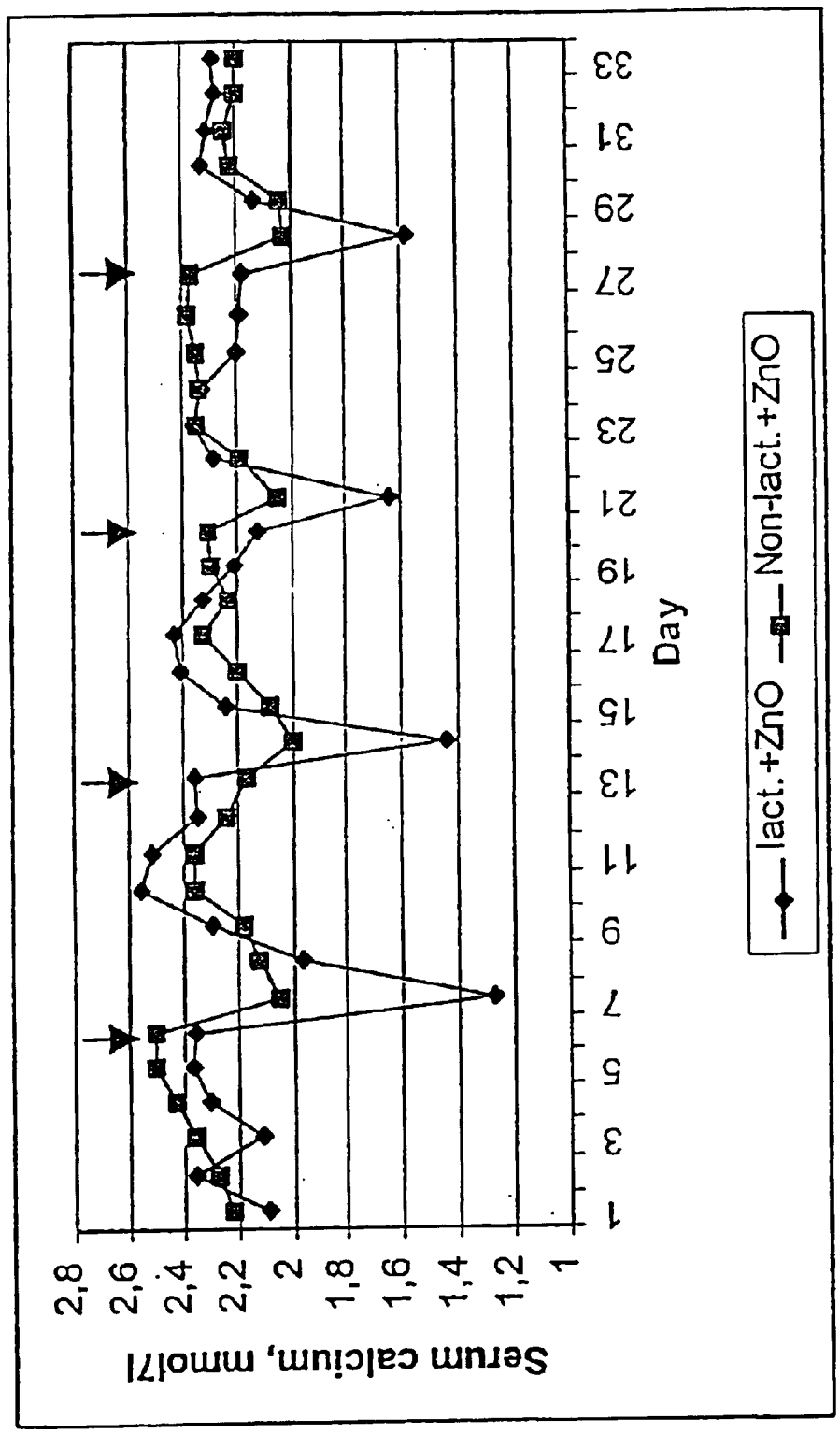
Figure 3:
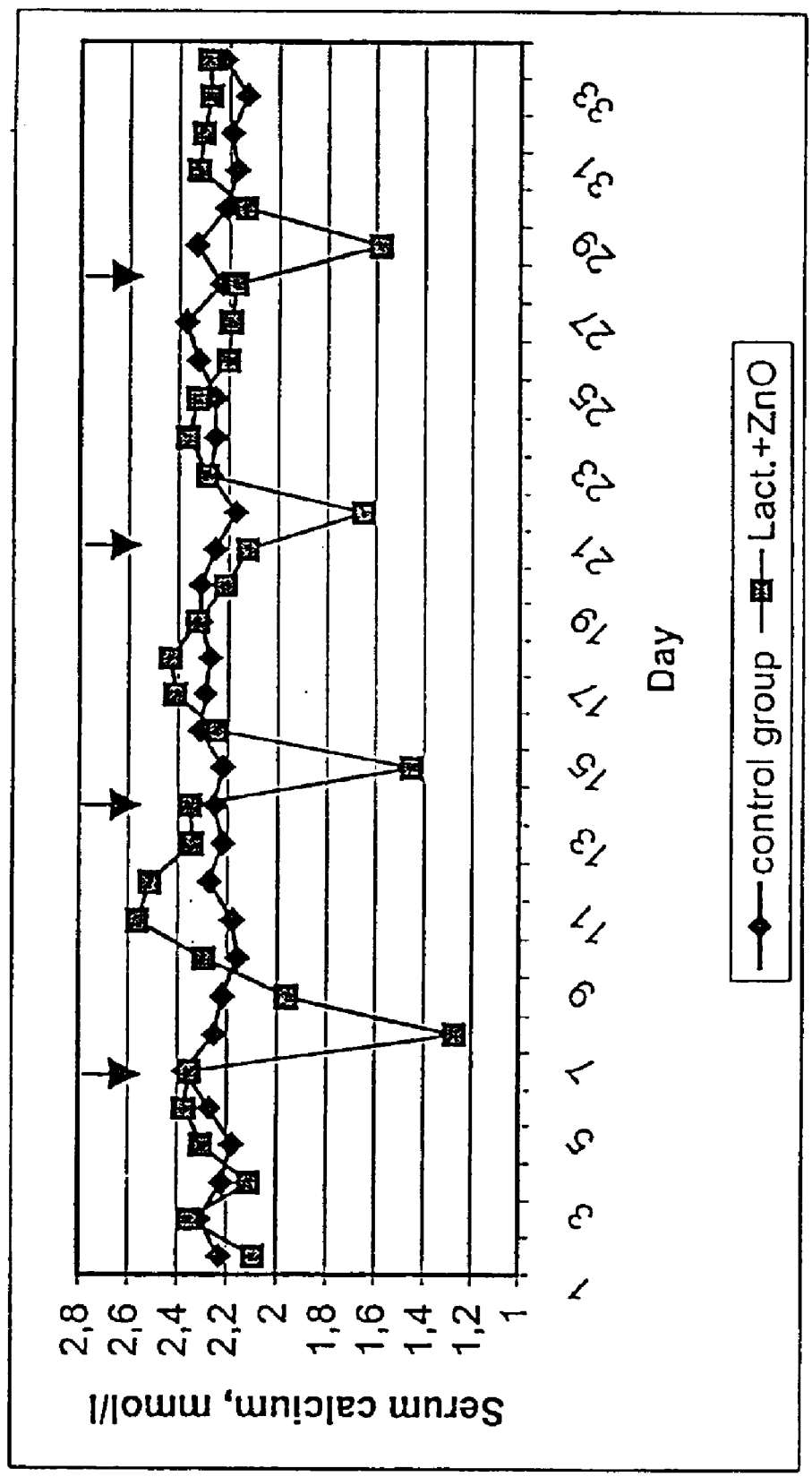
FIG. 3 shows the blood calcium concentration of the lactating cows given four doses of zinc oxide at one-week intervals, as well as of the non-lactating, untreated cows. Arrows indicate time of treatment.

FIG. 2 shows the response in serum calcium concentration of the lactating cows as well as of the non-lactating cows treated with the same amount of zinc oxide per kg of body weight. It is obvious that the most pronounced response was obtained in the lactating cows, followed by the dry cows. In the lactating cows the resulting hypocalcemia lasted about 24 hours with a minimum of 1.4–1.6 mmol/l occurring approx. 24 hours after administration. The minimum values were lower than the lowest accepted value for normal serum calcium concentration of 2.17 mmol/l (Rosol et al. 1995). In FIG. 3 the response of the lactating cows is shown more clearly on the background of the blood values of the untreated non-lactating controls. FIG. 4 shows that the response of the lactating cows to the zinc oxide doses changed with time, i.e. with the number of doses in that the cow's calcium balance became less and less affected.

2.4 Discussion

This experiment shows that hypocalcemic episodes of approximately 24 hours duration could be produced repeatedly in dairy cows by oral zinc oxide administration at one-week intervals. The graphs in FIG. 4 have a downward course. The fact that they are not horizontal shows that the cow's resistance to the induced hypocalcemia challenge increased with the number of zinc oxide induced hypocalcemic periods.

EXAMPLE 3

Repeated Administration of Synthetic Sodium Aluminium Zeolite A to Lactating Cows 3.1 Introduction So-called calcium binders are widely used in various industries such as the soap and detergent industry, or as water softeners in water treatment plants. Many natural minerals of the zeolite family as well as synthetic zeolites are strong cation exchangers and are used as such for the attraction of calcium in the form of $Ca^{2+}$ in exchange of other cations like sodium ($Na^{2+}$). In the following experiment a group of dairy cows were given such a zeolite and their serum calcium was monitored. The purpose was to test any direct effect on serum calcium during the drenching period as well as any delayed effect likely to be linked to resistance to hypocalcemia. In this experiment lactating dairy cows were used as a model for non-lactating (dry) cows.

3.2 Materials and methods

Five Red Danish Dairy cows in late lactation were used. The cows yielded approximately 20 kg of milk per day and were milked only once daily, i.e. in the morning. After an initial baseline period each cow received 0.5 kg of zeolite by stomach tube twice a day for two consecutive days. On the third day cows were only treated in the morning. In this way each cow received a total dosage of 2.5 kg. The zeolite used was a synthetic sodium aluminium silicate (Dedima 100; Degussa-Hüls AG, Germany). All cows were bleed twice a day: at 10 a.m. and at 22 p.m. Serum was stored at −18° C. and later analysed for total calcium concentration.

3.3 Results

FIG. 5 shows the average serum calcium response of the five cows. It can be seen that the serum calcium baseline values before administration fluctuated daily with comparatively low values in the morning followed by an increase during the day. During zeolite administration there was a repression in the increase in serum calcium during the day, as compared to before administration. From 24 hours after last administration and onwards full daily fluctuations were restored, but they now took place at a higher level as compared to the initial baseline level.

3.4 Discussion

This is a first testing of Dedima 100 in cows and it shows that at this dose level blood calcium is repressed during administration and that the animals respond to this by elevated calcium level after the administration period. The latter phenomenon is known from other descriptions of hypocalcemia and has been termed "overshooting" by Hove (1987) who describes it as a response to released parathyreoidea hormone (PTH) which is part of the organism's immediate defence mechanism against hypocalcemia.

EXAMPLE 4

Repeated Administration of Synthetic Sodium Aluminium Zeolite A to Dry Cows 4.1 Introduction The present experiment was performed with dry, non-pregnant cows as a model for dry, pregnant cows. Non-pregnant dry cows are expected to be less sensitive to hypocalcemia than pregnant dry cows because the former has the lowest requirement for calcium.

4.2 Materials and methods

Four non-pregnant dry dairy breed cows were used. Two of these were treated with Dedima 100 at a single dose of 2 kg/day for 4 days, whereas the other two served as untreated controls. Venous blood samples were taken daily from all four cows at 10.00 hours, i.e. two hours after morning feeding. Extra blood samples were taken on the days of administration at 22.00 hours.

4.3 Results

When compared with the untreated controls, a decrease in the concentration of the blood calcium was seen in the two experimental cows following the experimental treatment. As it can be seen from FIG. 6, in one cow (the zeolite 1-cow) this decrease in the concentration of the blood calcium was only slight and lasted only 1 or 2 days. In the other cow (the zeolite 2-cow) a more obvious decrease in blood calcium concentration was recorded. It was pronounced 2 days after the first dose was given and had reached 1.8 mmol/l by the third day after first administration and remained subnormal until 3 days after the last dose was given. There was a reduction in appetite in both the experimental cows and transient constipation was recorded in the zeolite 2-cow.

4.3 Discussion

This experiment demonstrates that hypocalcemia can be induced in a non-pregnant dry cow by the oral administration of a zeolite for 4 days. It also shows, that individual variation among such cows can be markedly. The recorded difference was similar to the difference seen in the same cows in a previous study (Example 2) with zinc oxide.

EXAMPLE 5

Prevention of Hypocalcemia in Calving Cows 5.1 Introduction

In a normal dairy cow population a proportion of the cows undergoes a period of hypocalcemia in relation to calving. As with milk fever the hypocalcemic period occurs 0–2 days post partum in most of these cows and its severity increase with increasing parity. In particular cows in 3rd parity and above are known to be prone to milk fever and subclinical hypocalcemia.

5.2 Materials and Methods

Fourteen non-lactating pregnant Jersey cows from the same herd were used in a controlled trial with a split herd design. All cows were fed the standard dry cow ration of the farm. In addition, 7 of the cows were exposed to the invention by receiving a premix in their feed, with calcium binding capacity (Na-aluminosilicate type A zeolite). The premix was given from 4 weeks prior to expected calving and until calving. All cows received calcium carbonate, 250 g per day, as an aquous suspension given by mouth in a bottle once daily at calving and the next two days thereafter. Blood sample no. 1 was taken at calving whereas sample 2 and 3 were taken one and two days after calving, respectively.

The effect of the invention, expressed as the difference between the blood sample results of the exposed and the non-exposed cows, was tested statistically. The results of the first two samples taken from each cow were included and processed by the statistical method PROC MIXED for Repeated Measurements (SAS Institute).

5.3 Results

Figure 7A:
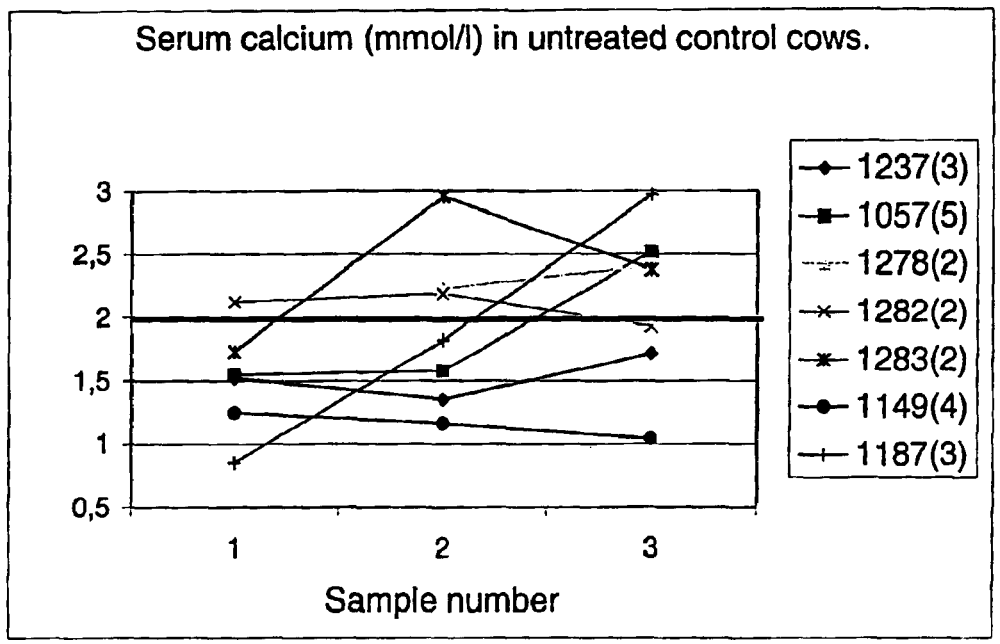
Figure 7B:
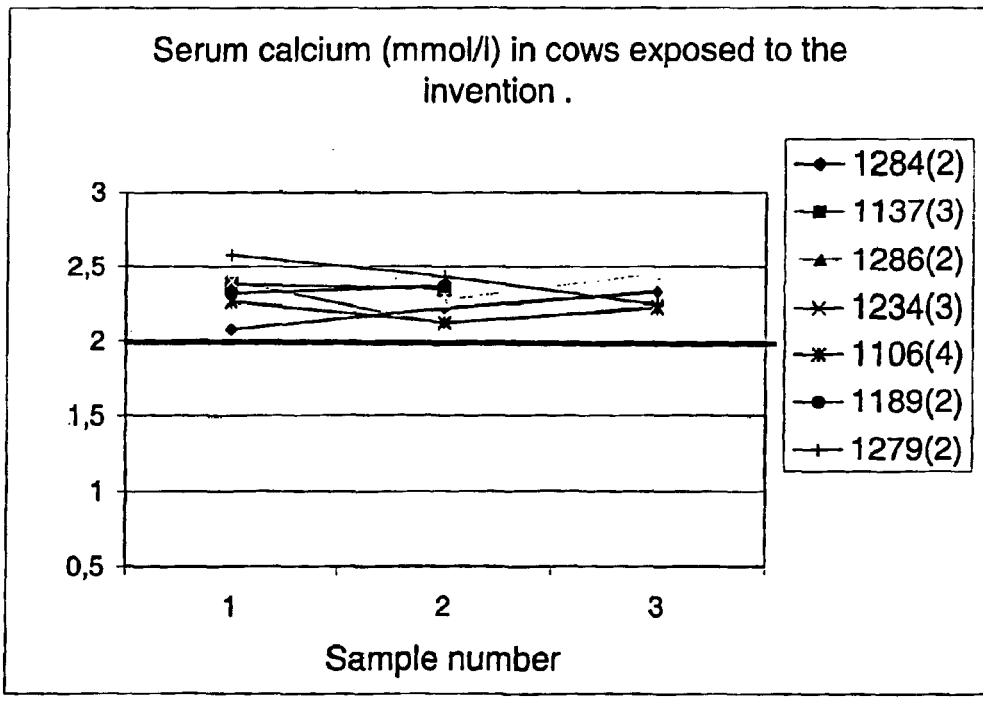

Individual cow results are shown in FIG. 7. Figures in brackets are parity numbers (no. of carvings) in that particular cow. As can bee seen from FIG. 7A the results of individual control cows were highly variable and in particular cows with higher parity numbers have blood calcium values below the critical value of 2 mmol/l (solid horizontal line) for hypocalcemia. Cows no. 1057, 1149 and 1187 contracted milk fever necessitating veterinary attendence and treatment with a calcium preparation in the blood, hence the drastic increases in some of the samples from these cows. FIG. 7B shows comparable results from the cows exposed to the invention. None of these cows experienced milk fever and, as can be seen, none of the sample results were below the critical value of 2 mmol/l for hypocalcemia. Milk fever as well as subclinical parturient hypocalcemia was thus completely prevented. The difference between the unexposed cows in figure A and the exposed but otherwise comparable cows in figure B is obvious and statistically highly significant (p-value<0.01).

5.4 Discussion and Conclusion

It is concluded that exposure of the cows to the invention completely prevented milk fever as well as subclinical parturient hypocalcemia. This effect should be seen in relation to the efficiency of the presently most used preventive principle, acidification of dry cows by anion supplementation to their feed ration, which is only partial and reach a maximum of 50–60% only. Without being bound by the hypotheses behind the present invention, its efficiency may be characterised as surprisingly high.

REFERENCES

Dishington, I. W. and Bjoernstad, J. 1982. Prevention of milk fever by dietary means. The effect of a concentrate fortified with mineral salts. Acta vet. scand., 23, 336–343.

Hove, K. 1987. Milk fever prevention and calcium homeostasis around calving in the Dairy cow. Agripractice; Irish Veterinary news, March 1987:24–27.

Jorgensen, R. J., Basse, A. and Asian, V. 1990. Sequelae to oral calcium chloride gel dosing of cows. Proceedings, XVI World Buiatrics Congress, 13–17. August 1990, Salvador, Bahia, Brazil, pp. 511–515.

Jorgensen, R. J., Nyengaard, N. R., Daniel, R. C. W., Mellau, L. S. B., Enemark, J. M. D. 1999. Induced hypocalcaemia by $Na_2EDTA$ infusion. A review. Journal of Veterinary medicine A, Vol. 46(7):389–452.

Mellau, L. S. B., Jorgensen, R. J., Enemark, J. M. D. 1998. Standardization and interpretation of experimental (Na2EDTA induced) hypocalcaemia in cows. $10^{th}$ ICPD (International Conference on Production Diseases in Farm Animals), Utrecht, p. 238.

Ramberg, C. F., Phang, J. M. and Kronfeld, D. S. 1970. A compartmental model of calcium metabolism in cows. In: Parturient hypocalcemia. Academic Press, New York, pp. 119–134.

Rosol, T. J., Chew, J. D., Nagode, L. A., Capen, C. C. 1994. Pathophysiology of calcium metabolism. Veterinary Clinical Pathology, 24:49–63.

Smith, B. L., Collier, A. J., Lawrence, R. J., Towers, N. R. 1984. Hypocalcaemia associated with high dose rates of zinc oxide to lactating dairy cows. New Zealand Veterinary Journal, 32:48–50.

Van't Klooster, A. Th. 1976. Adaptation of calcium absorption from the small intestine of dairy cows to changes in the dietary calcium intake and at the onset of lactation. Z. Tierphysiol., Tieremährg. u. Futtermittelkde, 37:169–182.

Wang, C. and Beede, D. K. 1992. Effect of ammonium chloride and sulphate on acid-base status and calcium metabolism of dry cows. Journal of Dairy Science, 75:820–828.

What is claimed is:

1. A composition for preventing parturient hypocalcemia in an animal, comprising, in a suitable form for peroral administration, at least one calcium-binding compound which is a zeolite, said compound(s), provided in an amount effective to reduce the absorption of calcium from the drinking water and/or from the ration of said animal wherein the compound is encapsulated by a calcium-free membrane material which is a cellulose.

2. The composition according to claim 1 wherein the compound has a competitive effect on the absorption of calcium from drinking water and/or from the ration of the animal.

3. The composition according to claim 1, wherein the compound is in the form of granules, pellets, or tablets.

4. The composition according to claim 1 where the composition is in the form of a premix, a liquid and a powder.

5. The composition according to claim 4 where the composition is added to the drinking water and/or to the ration of the dry animal.

6. The composition according to claim 1 where the composition comprises at least one further ingredient.

7. The composition according to claim 1 where the composition is calcium-free and non-acidifying.

8. The composition according to claim 1, comprising two different compounds which reduce the absorption of calcium from the drinking water and/or from the ration of said animal.

9. The composition according to claim 8, wherein one compound is a zeolite, and the other compound is selected from the group consisting of oxalic acid, sodium oxalate, phytic acid, a phytate, a clay mineral, ethylenediaminetetraacetic acid (EDTA) and its sodium salts $Na_2EDTA$ and $Na_4EDTA$, trisodium nitrilotriacetate monohydrate, trisodium nitriloacetate, pentasodium diethylenetriaminepentaacetate, trisodium N-hydroxyethylethylenediaminetriacetate, citric acid, a citrate, a polyphosphate, a tripolyphosphate, an orthophosphate and a cellulose phosphate.

10. The composition of claim 1 where said membrane material, at the body temperature of the lactating animal, is solid at a pH value above 4.0, and dissolves at pH below 4.0.

11. A method of preventing parturient hypocalcemia in an animal, comprising administering to the animal during at least part of the dry period an effective amount of a composition according to claim 1.

12. The method according to claim 11, wherein the compound is administered perorally.

13. The method according to claim 1, wherein the calcium-binding compound is synthetic sodium aluminosilicate zeolite type A.

14. The method according to claim 11, comprising administering to the animal during at least part of the dry period an effective amount of a compound which has a competitive effect on the absorption of calcium from the drinking water and/or from the ration of said animal.

15. The method according to claim 11 wherein the compound is contained in a composition which is in the form of a premix, a liquid and a powder.

16. The method according to claim 15 wherein the composition is added to the drinking water and/or to the ration of the dry animal.

17. The method according to claim 12, wherein at least 10 g of the compound is administered to the animal daily.

18. The method according to claim 17, wherein at least 50 g of the compound is administered daily.

* * * * *